United States Patent [19]
Bittner

[11] 4,366,701
[45] Jan. 4, 1983

[54] OCTANE MEASURING

[75] Inventor: John M. Bittner, Trenton, N.J.

[73] Assignee: Ethyl Corporation, Richmond, Va.

[21] Appl. No.: 159,512

[22] Filed: Jun. 16, 1980

Related U.S. Application Data

[63] Continuation-in-part of Ser. No. 61,473, Jul. 27, 1979, Pat. No. 4,276,770.

[51] Int. Cl.³ ............................................ G01N 33/22
[52] U.S. Cl. ...................................... 73/35; 318/592
[58] Field of Search .................... 73/35; 364/450, 451, 364/508; 318/592

[56] References Cited

U.S. PATENT DOCUMENTS

| | | | |
|---|---|---|---|
| 3,490,719 | 1/1970 | Cantor et al. | 318/592 |
| 3,614,888 | 10/1971 | Jones et al. | 73/35 |
| 3,690,851 | 9/1972 | Jones et al. | 73/35 X |
| 4,153,020 | 5/1979 | King et al. | 73/35 X |

Primary Examiner—James J. Gill
Attorney, Agent, or Firm—Donald L. Johnson

[57] ABSTRACT

Automatic octane measurements are made very rapidly with standard test engine using an all-electronic control that automatically lowers the fuel-air ratio to bring the knock intensity below standard, then automatically adjusts the compression to bring the knock intensity to standard, then intermittently increases the fuel-air ratio, after the first or second intermittent increase permits automatic compensatory compression changes only in the decreasing direction to compensate for departures from standard knock intensity and conducts these compensatory compression changes at a rate too slow for adequate compensation if the fuel-air ratio increase causes a substantial increase in knock intensity, and then indicating the compression ratio reading after the knock intensity remains standard during two to four successive fuel-air ratio increases. Maximum knock fuel-air ratio is indicated by subsequently automatically lowering the fuel-air ratio an amount corresponding to the fuel-air ratio increases during which knock intensity remained at standard. Finally for some purposes the test engine can be permitted to stabilize at the maximum knock fuel-air ratio. Electronic memory can be used to translate compression ratio to octane number, and barometric correction can be made electronically.

2 Claims, 7 Drawing Figures

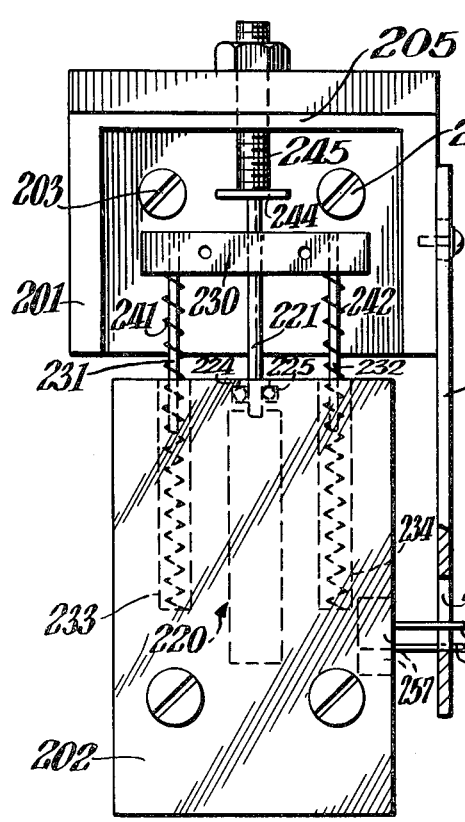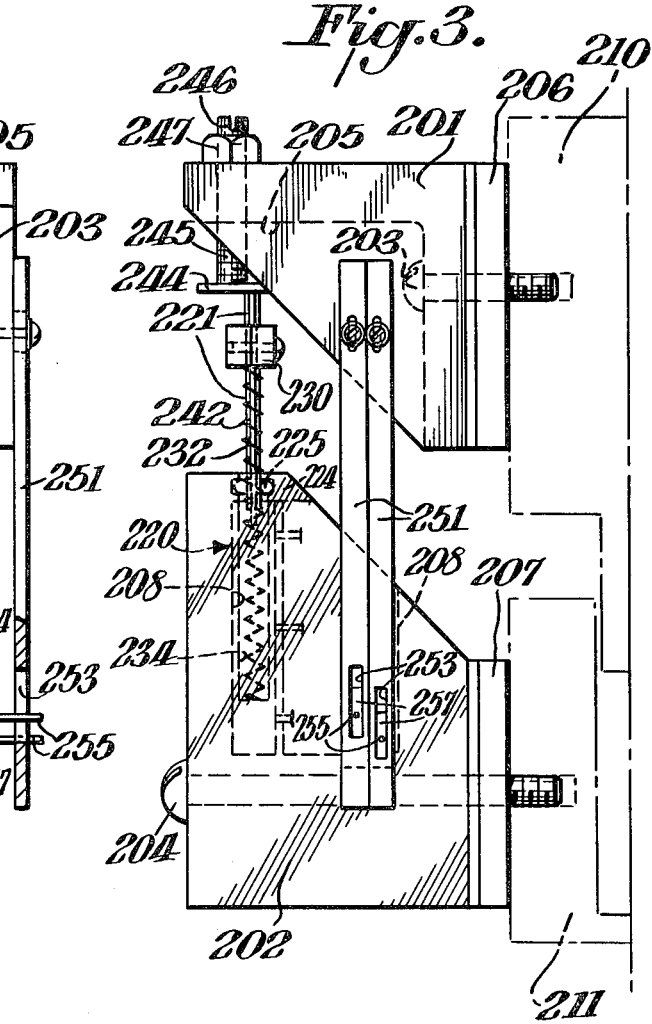

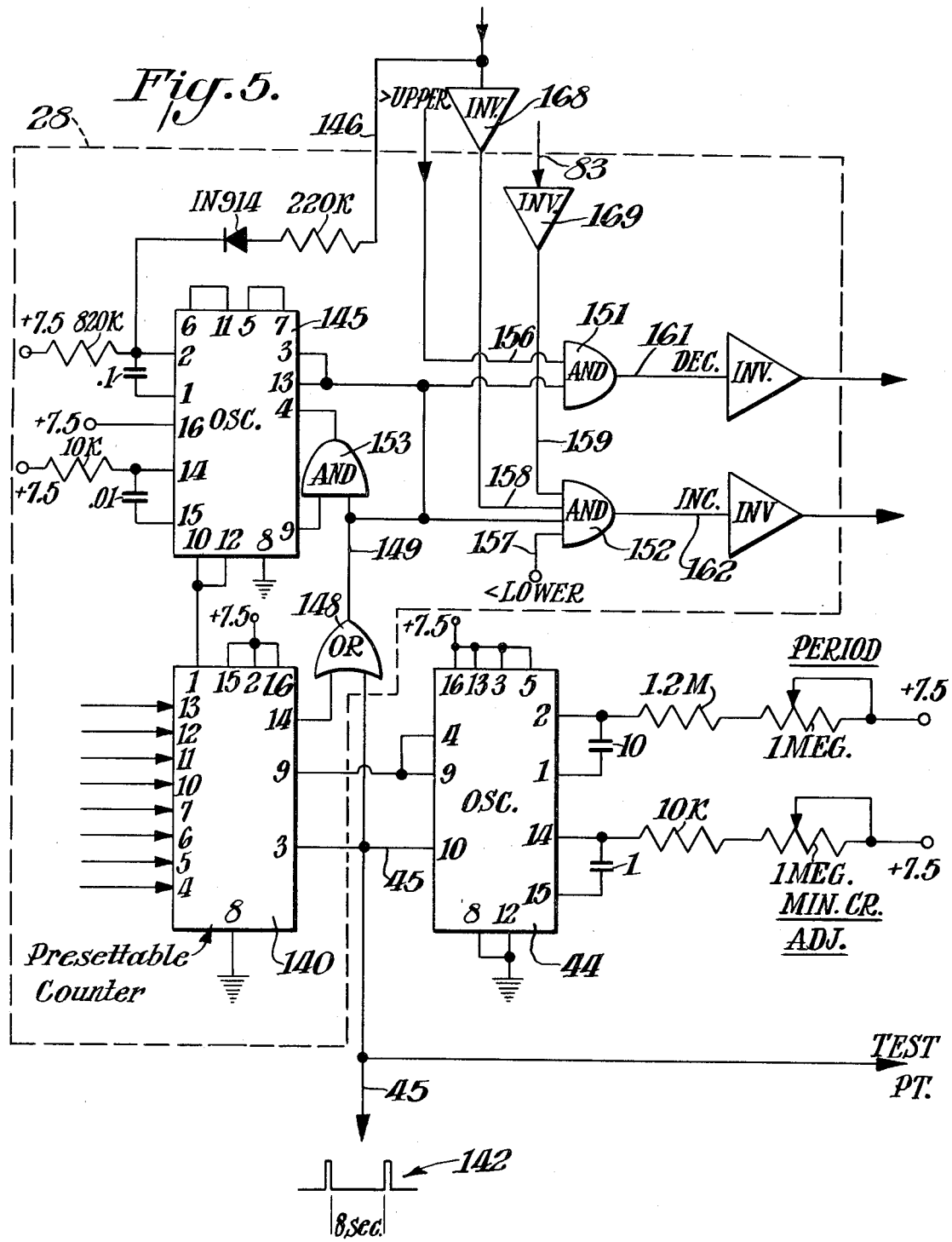

OCTANE MEASURING

This application is a continuation-in-part of application Ser. No. 61,473 filed July 27, 1979 (U.S. Pat. No. 4,276,770 granted July 7, 1981).

The present invention relates to determining octane ratings.

Among the objects of the present invention is the provision of octane rating determining apparatus and processes which are improvements over prior apparatuses and processes such as those shown in U.S. Pat. Nos. 3,383,904, 3,488,168, 3,596,281, 3,614,888, 3,621,341, 3,661,540, 3,690,851, 3,913,380, 3,456,492 and 3,949,595.

The foregoing as well as additional objects of the present invention will be more fully understood from the following description of several of its embodiments, reference being made to the accompanying drawings wherein:

FIG. 3 is a side view of an attachment for a test engine for use with octane rating determination;

FIG. 4 is a front view of the attachment of FIG. 3;

FIG. 5 is a circuit diagram for an automatic compression correction pulse generator of the present invention.

The official octane rating system calls for the use of a standard test engine, described for example in the 1977 Annual Book of ASTM Standards, Part 47, published by American Society For Testing and Materials, having a variabe compression ratio and a knock intensity output signal. As noted in the above-numbered prior patents it has been found convenient to place a sample of the fuel to be tested in a bowl of the engine's carburetor, switch the engine to that fuel, perform an initial compression ratio adjustment to bring the knock intensity to the desired standard, then make a fuel-air ratio search to find the ratio at which the fuel produces maximum knock, and make a final compression ratio correction to bring the knock intensity to the standard value. This entire sequence can be carried out automatically but takes an average of over 5 minutes, and has required the use of slow-moving mechanical peak-picking equipment peculiarly adapted to the idiosyncracies of standard test engines.

According to the present invention, the fuel-air ratio search is made by first lowering that ratio, adjusting the compression ratio to bring the knock intensity to standard, and finally increading the fuel-air ratio in intermittent steps while permitting automatic compensatory changes of compression ratio in the downward direction only and at a correction rate too slow for adequate compensation if these increases effect substantial increases in knock intensity. The entire rating sequence is completed when the knock intensity remains at the desired standard during two to four successive fuel-air ratio increases, without a compression ratio change.

Nothing further need to be done to obtain accurate and highly reproducible Research Octane ratings and the average time required is less than four minutes, sometimes as low as two minutes. Moreover no mechanical peak-picking is needed so that the equipment can be essentially entirely electronic and highly compact.

The fuel-air ratio will overshoot the desired maximum-knock value, particularly if the intermittent bowl raisings are each about 0.01 or more inches, so that if the maximum-knock fuel-air ratio is to be also determined, the bowl is lowered at the end of the sequence by an amount corresponding to some or all of the amount raised after the last compression ratio change.

Moreover where the bowl raisings are each greater than 0.01 inch, the final compression ratio reached after a Motor Method octane sequence is sometimes not reliable unless it will maintain itself for at least about 30 seconds. When carrying out a Motor Method sequence it is accordingly helpful to keep the equipment operating in 20-second stages after the initial end-point determination, and preferably after the bowl is lowered to compensate for the above-noted overshoot, until no compression ratio change takes place during such a stage.

Figure 1:
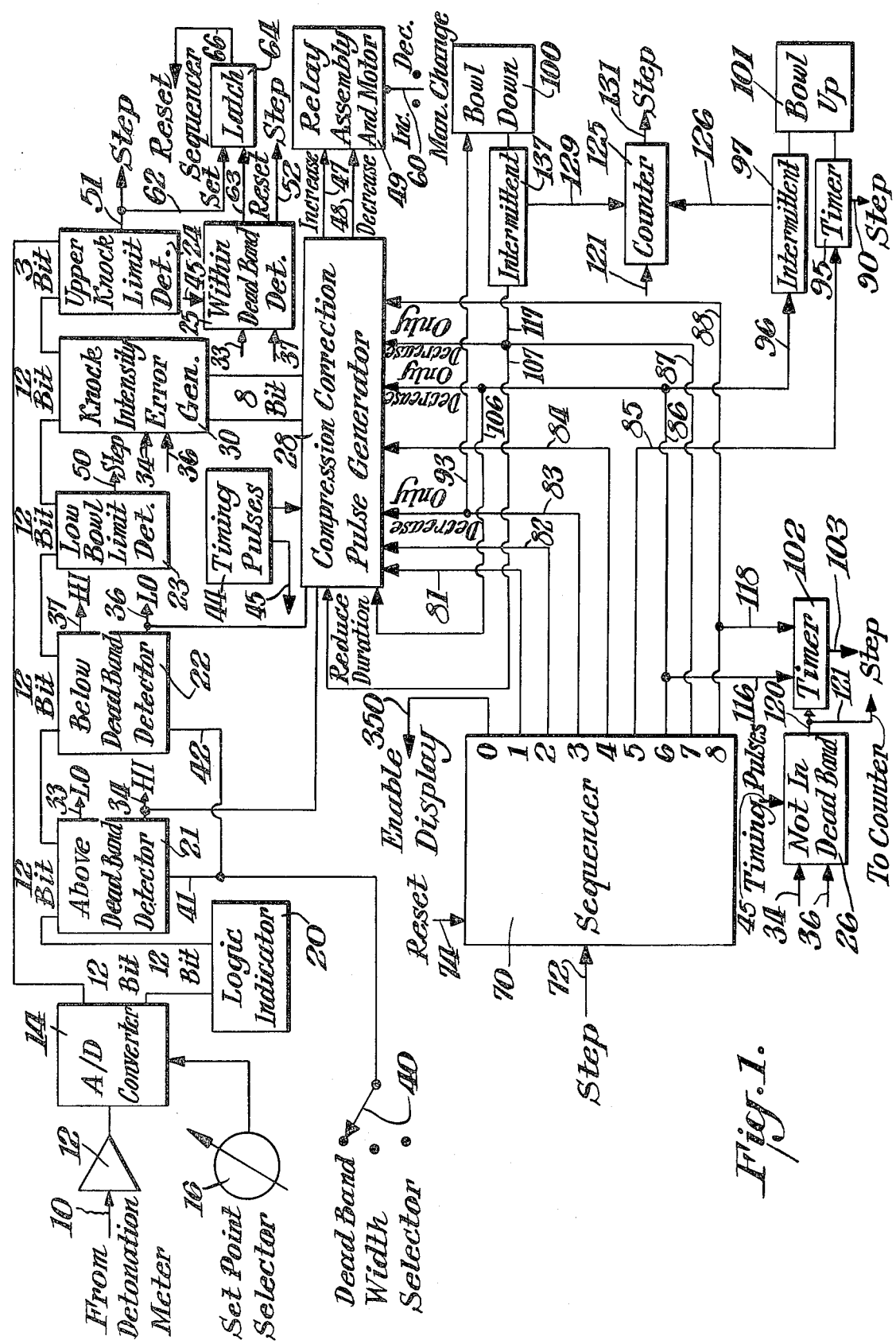
FIG. 1 is a block diagram showing the key electrical features of an apparatus exemplifying the present invention.

Turning now to the drawings, FIG. 1 shows an apparatus that receives signals at 10 from the knockmeter of a standard test engine, and with the help of an amplifier 12 the signals are converted in analog-to-digital converter 14 to a 12-bit digital output. The knockmeter signals are generally zero to 12 millivolts d.c. analog voltages corresponding to the intensity at which knocking occurs in the test engine. These signals are preferably damped by the minimum amount of damping provided in the standard knockmeter, and amplified to zero-to-10-volt d.c. analog signals for delivery to standard analog-to-digital converters. A set point selector in the form of a potentiometer 16 can be connected to supply a signal level set point, generally a fixed value between 45 and 55 on the zero-to-one-hundred knock intensity scale of the knockmeter. The digital output of the converter is a binary representation of the knock intensity and is offset by the set point selector.

That digital output is supplied to a group of detectors 21, 22, 23 and 24, and to a knock intensity error generator 30. The output can also be supplied to a logic indicator 20 for displaying the knock intensity signal as for example for trouble shooting in the event the apparatus misoperates.

Detector 21 compares the 12-bit signal from the converter with the upper limit of a dead band width signal received at 41 from a Dead Band Width Selector 40 that by way of example can select bands corresponding to ±1, ±2 or ±3 scale widths on the knockmeter scale. A small dead band, at least about 1 scale unit wide, is needed to reduce hunting, but wider dead bands enable more rapid though coarser octane rating determinations. It is generally desirable to select a dead band width corresponding to the extremes of fluctuation that the test engine undergoes when operating. Detector 21 has two outputs, 33 and 34 which carry signals when the 12-bit knock signals correspond to magnitudes below or above the upper dead band limit, respectively.

Detector 22 similarly compares the 12-bit knock signals with the dead band width signals and shows at its outputs 36 and 37 whether the knock intensity is below or above the low end of the selected dead band.

Detector 23 compres the knock intensity signals with a pre-determined minimum known intensity, and delivers at 50 a signal showing that the knock intensity is below that limit. Such a limit can be fixed at 4 units below the dead band on the knockmeter scale, or at any other value desired for efficiently carrying out the octane determining sequence. In the illustrated embodiment the signal at 50 is used to automatically terminate the downward movement of the carburetor bowl as described infra.

Detector 24 compares the knock intensity signal with a limiting knock intensity setting that should not be exceeded by the test engine. Excessively violent knocking can damage the test engine, and detector 24 can be arranged to deliver an out signal at 51 when the knock intensity reaches a value corresponding to 87 or thereabouts on the standard knockmeter scale. Only the signals from the three most significant bits of the 12-bit knock intensity signals need be supplied to detector 24 with such settings.

Generator 30 is supplied not only with the 12-bit knock intensity signals, but also with the signals from 34 and 36. It compares the measured knock intensity with the upper and lower limits of the dead band, and puts out an 8-bit digital signal corresponding to the magnitude of the departure of the knock intensity from the dead band. This 8-bit error signal is supplied to a Compression Correction Pulse Generator 28.

Generator 28 also receives the signals from 34 and 36 as well as timing pulses from a timing pulse generator 44. When generator 28 is actuated, it will at each timing pulse produce a compression correcting pulse of variable length such as from about 0.1 to about 8 seconds each. The exact length of the correcting pulse will vary with the magnitude of the 8-bit error signal, and will be delivered to an Increase or Decrease output line 47 or 48 depending upon whether generator 28 is receiving a below-dead-band signal 36 or an above-dead-band signal 34. The Increase and Decrease signals operate a relay and motor combination 49 such as is generally provided in standard test engines to increase or decrease the compression ratio of the test engine. The minimum correcting pulse length is preferably set at the value that causes the motor to make the minimum change in compression ratio. A manual control 60 for compression ratio changes is also desirable.

A sequencer 70 controls the octane rating determination. It is shown as having nine output connections, numbered from zero through 8, and can be a simple ring counter that shifts from one output to the next at each counting step. A stepping input is provided at 72, and a reset to zero provided at 74. The various outputs are connected to the Compression Correction Pulse Generator, to the motor that moves the carburetor bowl up and down, as well as to various timers, as illustrated, with the zero output connected to enable the display of octane number.

KNOCK LIMITING OPERATION

With the apparatus connected to a test engine that is running, and with the control of FIG. 1 energized so that it will operate when needed, no sequencing is taking place and the sequencer output is at the zero terminal. This keeps an octane display readout enabled so that octane numbers can be read if for example the equipment is being operated manually. No aspect of manual operation is obstructed. The equipment can be maintained in this standby condition, with the engine operating, so that it is ready for immediate use to determine octane numbers.

However with no one paying much attention to the equipment, it is possible for a change of fuel to cause the engine to knock at high intensity, sufficiently high to damage the engine if not promptly corrected. This high intensity is detected by detector 24 which then puts out a step signal at 51. The step signal is delivered to step input 72 of the sequencer by a circuit that is not illustrated, and shifts the sequencer output to its terminal 1. The octane display is accordingly disabled, and the Compression Correction Pulse Generator 28 is actuated through line 81. Accordingly the next timing pulse from timing pulse generator 44 triggers a Decrease correction signal which is delivered to assembly 49, and the compression change motor is actuated to reduce the compression ratio of the test engine. This triggering and compression ratio reduction repeats itself so long as the knock intensity exceeds the upper limit of the dead band, although as the knock intensity is lowered toward that dead band limit the correction pulses become shorter in length. The first compression ratio decrease signal responds to a very large knock error and can have a duration so long as to continue until the next timing pulse, in which event the motor effecting compression ratio decrease is continually actuated during the interval between successive timing pulses, or even through three or more successive timing pulses.

When the knock intensity falls sufficiently to enter the dead band, the compression ratio reduction is automatically terminated. This is shown in FIG. 1 by a resetting of the Sequencer 70. Upper Knock Limit signal 51 is illustrated as not only actuating the stepping of the sequencer, but is also connected through lead 62 to set an electronic latch 64 that has an output line 66. When set there is no signal on that output line. The latch also has a reset input 63 which is actuated by the output of a detector 25 connected to lines 33 and 37 to detect when the knock intensity is within the dead band. When that happens this detector actuates the reset 63 of latch 64, and since the set input 62 for that latch has been deactuated, the latch resets. Upon resetting this latch energizes its output 66 which is connected to the reset input 74 of the sequencer, and the sequencer is thus caused to reset to its zero output.

The apparatus accordingly safeguards the test engine, and does this even if the equipment is completely unattended.

AUTOMATIC OCTANE RATING

To conduct an automatic octane rating determination on a fuel when the equipment is in the foregoing standby condition, it is only necessary to have that fuel supplied from a bowl of the engine's carburetor, and to then step the Sequencer 70 into its 1-output. For this purpose a manual ON switch, not shown, can be momentarily closed to deliver a stepping pulse to stepping input 72. In the 1-output condition the sequencer activates the Compression Correction Pulse Generator (again through line 81) so that the timing pulses from timing pulse generator 44 trigger compression ratio correction pulses if the knock intensity is not in the selected dead band. The first timing pulse after the knock intensity reaches the dead band will cause the Within Dead Band Detector 25 to deliver a step signal from a second output 52 which is supplied to the sequencer stepping input 72. The reset signal 63 which is simultaneously generated by detector 25 does not actuate the sequencer reset inasmuch as the latch 64 is not set.

Sequencer 70 is accordingly stepped to its 2-output. Here the Compression Correction Pulse Generator 28 is actuated through line 82 so that the automatic compression ratio operation continues to the next timing pulse from 44. If at that pulse or at a succeeding pulse, the knock intensity is in the selected dead band, the sequencer stepping is repeated and the sequecer shifts into its 3-output.

The 3-output actuates generator 28 through line 83, and through a branch line 93 also actuates the down winding 100 of the motor for the test engine's fuel bowl, to lower that bowl. However the actuation of generator 28 by line 83 only permits that generator to deliver decrease output signals.

The downward movement of the fuel bowl reduces the fuel-air ratio of the combustion mixture supplied to the test engine, and the knock intensity will diminish. It is possible for the knock intensity to increase before it starts to diminish, inasmuch as the bowl might have originally been at a level that supplied the fuel at a fuel-air ratio higher than its maximum knock ratio. The bowl lowering will in such a situation first bring that ratio through maximum knock. The resulting transient increase in engine knock intensity may trigger a compression decrease signal but will be otherwise ignored by the apparatus.

Even a transient knock intensity increase to the value that would otherwise trigger Upper Knock Limit Detector 24, can be ignored as by disabling step output 51 of that detector when the sequence is in its 3-output stage. Thus output 51 can be supplied through an AND gate that is only enabled when the Sequencer 70 is in its standby condition and activating its own zero-output terminal.

Lowering the bowl at the rate of about 4/10 inch per minute provides very good operation, but other rates from about ⅛ to about ⅝ inch per minute can also be used.

The down movement of the fuel bowl proceeds until the knock intensity diminishes to the level that triggers Low Bowl Limit Detector 23. Such triggering generates a stepping output at 50, which output is supplied to the stepping input 72 of the sequencer, and the sequencer is thus stepped to its 4-output condition. In this condition the Compression Correction Pulse Generator 18 is actuated through line 84. This actuation is an unrestricted actuation such as takes places with line 81 and 82, and causes the compression ratio of the test engine to be automatically brought to the point at which the knock intensity is in the selected dead band. This automatic change amounts to an increase in compression ratio, and if desired can be effected with the generator 28 actuated only to deliver Increase signals at its output 47.

The return of the knock intensity to the dead band causes the next timing pulse from generator 44 to trigger another stepping signal at the output 52 of the Within Dead Band Detector, and this steps the Sequencer 70 to its 5-output condition. Here the sequence's 5-output line 85 actuates through a timer 95, the up winding 101 of the bowl motor to raise the bowl. The bowl is lifted about 0.10 to about 0.20 inches, preferably 0.15 inches, something easily effected in about 10 to 20 seconds, after which timer 95 times out and delivers a stepping signal to an output line 90. This stepping signal is supplied to step input 72 of Sequencer 70 and steps it to its 6-output condition.

If the downward bowl movement is prolonged, for example because the Low Bowl Limit Detector is set for a very low limit, or because the bowl motor lowering is so rapid that the test engine's knockmeter output lags excessively, the rising of the bowl motor in the 5-output condition can also be prolonged or can be made in two steps.

In the 6-output condition Sequencer 70 actuates, through output line 86 and branch line 96, the intermittent further raising of the fuel bowl. To this end a pulse generator 97 is connected for actuation by line 96, and also connected to deliver its generated pulses to the up winding 101 of the bowl motor. These pulses are preferably two seconds long spaced 8 seconds apart, but the bowl steps can be from about 0.15 to about 0.05 inch each with pauses at least about six seconds long to permit the test engine to stabilize itself after each bowl step. The duration of each step can also be reduced to one second or even less if desired, inasmuch as this will speed the octane measurement. Pauses over about 10 seconds long between pulses, unduly delay the measurement.

The 6-output line 86 is also connected to actuate Compression Correction Pulse Generator to deliver decrease signals only, and in addition an auxiliary line 106 supplied by output line 86 is shown connected to reduce the duration of each Compression Correction pulse while Sequencer 70 is in its 6-output condition. Such a reduction is typically from about 1/6 to about ½, preferably about ¼, the normal correction pulse width. Each normal pulse can, by way of example, effect a cylinder head movement at the rate of about 0.0005 to about 0.002 inches per second of pulse length, although the first 0.05 to about 0.3 second of a correction pulse is generally consumed in releasing a brake on the compression ratio change motor, or in other electrical delays. Only the balance of each pulse is actually devoted to compression ratio change.

Finally the 6-output line has another branch 116 which starts a timer 102 operating. This timer is also connected by line 120 to a Not In Dead Band Detector 26 which causes the timer to be reset whenever a timing pulse from Timing Pulse Generator 44 shows that the test engine's knock intensity is not within the selected dead band. Connection by line 45 to that Generator, and by lines 34 and 36 to Detectors 21 and 22, effect such operation.

Timer 102 can have a timing run of about 15 to about 30 seconds, preferably about 20 to 21 seconds, and has a stepping output at 103 to step Sequencer 70 to its next output position when the timer times out. Also Detector 26 has an additional output line 121 connected to reset a counter 125 when it resets timer 102. Counter 125 counts pulses delivered by pulse generator 97 through line 126.

It is preferred that the timing run of timer 102 be long enough to show that the knock intensity of the test engine is within the desired dead band during two to four successive up movements of the fuel bowl. Such movements of 0.025 inch each or even as little as 0.015 inch each, will be enough to assure that the fuel-air ratio has become enriched to the point that it has passed through the maximum knock ratio and the knock intensity is no longer increasing with further enrichment. Indeed only two upward steps of about 0.025 inch each are usually sufficient for this purpose.

The test engine's knock intensity goes through a maximum or peak as the fuel-air ratio is increased, and when suitable increases are made to an excessively lean ratio the knock intensity generally increases with each fuel-air ratio increase until the ratio is very close to or at the peak ratio. Each knock intensity increase will generally also cause a compression correction pulse that decreases the compression ratio of the test engine and thus also decreases the knock intensity, keeping it in or just above the dead band. When two successive fuel-air ratio increases of this type do not increase the knock intensity sufficiently and the knock intensity remains below the upper limit of the dead band, the peak fuel-air ratio has been overshot slightly.

Timer 102 has a timing run that spans at least two successive fuel-air ratio increases, so that the continued absence of a resetting signal from detector 26 during such a time span permits this timer to time out and generate a stepping signal at 103. This steps Sequencer 70 to its 7-output position and stops further increases in the fuel-air ratio. Also the same absence of that resetting signal has permitted counter 125 to count the number of fuel-air ratio increases that have been effected with the knock intensity in the dead band. This generally corresponds to the overshoot of the fuel-air ratio increases.

In output stage 7, the sequencer effects a lowering of the fuel bowl to compensate for the overshoot. The Compression Correction Pulse Generator is again connected, through line 87, to generate decrease signals only. Also line 107 branched from line 87, reduces the duration of the compression correction pulses that are generated, corresponding to the reduction effected by line 106 in sequencer output 6.

A pulse generator 137 similar to generator 97 is actuated by line 117 branched from line 87, and generator 137 supplies its pulses to the down windings 100 of the bowl motor. These pulses do not have to be spaced apart more than about 0.1 second, and are preferably just as long as the bowl-lifting pulses from generator 97 so that the up and down windings of the bowl motor can be identical. If desired these bowl-down pulses can be made slightly more or less effective than the bowl-up pulses, in order to have the bowl-down compensation travel 10% or so more or less than the bowl-up travel to be compensated, and thus more accurately compensate for the overshoot of maximum knock ratio.

Line 129 delivers the bowl-down pulses to counter 125 and causes that counter to count down. When the count-down equals the count previously reached at the end of the bowl-up travel, counter 125 delivers a stepping signal at an output 131. This steps Sequencer 70 to its 8-output.

In its 8-output stage Sequencer 70 energizes the Compression Correction Pulse Generator through line 88 and also energizes timer 102 through line 118. This permits the test engine to run a little longer without a fuel-air ratio change to make sure the engine is fully stabilized. When making Motor Octane ratings the knock intensity sometimes changes during such stabilizing run and causes the generator of a compression correction pulse. Such a pulse will cause detector 26 to reset timer 102.

When timer 102 times out during the 8-output stage of Sequencer 70, it again generates a stepping signal at 103, and this steps Sequencer 70 to its O-position where it enables the display of an octane number readout corresponding to the final position of the test engine's cylinder head. The octane number so displayed has been found highly reproducible and closely correlated with octane numbers determined by the non-automatic method described in the ASTM Standards publication.

When conducting a Research Octane measurement the test engine does not need further stabilization after the completion of stage 6 in the sequencing. Stages 7 and 8 can then be eliminated altogether, although stage 7 can be retained if it is desired that the fuel-air ratio at the end of the measurement be accurately fixed at the maximum knock ratio.

Suitable blocking provisions can be incorporated, for example to keep step output 52 from actuating Sequencer 70 every time the knock intensity is within the selected dead band. Thus the reset line 52 can be fed through an AND gate having a second input that is only energized when Sequencer 70 is in its stages 1 or 2.

Some or all of the sequenced operating steps can be arranged to trigger the next step without going through the sequencer. For instance the line 52 can have a branch connected through an AND gate to start timer 95 when that AND gate also receives an input from line 50. In such a variation sequencer stage 5 can be omitted.

Only about 3 minutes time is consumed by the octane determination, less if the test engine at the start of the determination is operating at a knock intensity close to the selected dead band. When it also happens to be operating with its carburetor bowl at a level close to that which actuates the low bowl limit detector 23, the total time for an octane determination can be as little as 2 ½ minutes.

The use of the 7th and 8th sequencer stage adds about ½ minute to a determination.

As pointed out above the raising of the carburetor bowl is preferably effected in steps with a sufficient pause between steps to permit the test engine to stabilize its operation at the particular level of the last step. The first upward step of the bowl can be a large one, as much as five to ten times the later steps inasmuch as the bowl is moving up from a position so low that even the fuel with the leanest maximum knock fuel-air ratio will require a substantial raising of the bowl.

Where the bowl lowering is to a very low level, as for example when the lowering is related to the lower limit of the dead band and the selected dead band is very wide, the first bowl-up step can be made somewhat greater. This step can in such situations be under the control of the dead band selector.

Instead of controlling fuel-air ratio by carburetor bowl height, other techniques can be used. Indeed when making octane measurements of gaseous fuels such as liquefied natural gas or other light hydrocarbons, such bowl height control cannot be used. The fuel and air can then be supplied to the engine intake through bleed valves operated by electric motors that take the place of the carburetor bowl motor in the arrangement of FIG. 1.

Test engines generally respond more rapidly to mixture enrichment steps than to mixture leaning steps and so it is desirable to do the maximum knock fuel-air ratio determination in steps of mixture enrichment rather than steps of mixture leaning. By making the pauses between steps several seconds longer, the maximum knock fuel-air ratio determination can be conducted with mixture-leaning steps and this adds about ½ minute to the octane measurement sequence time.

The sequence time can be generally reduced by keeping the automatic engine compression correction in full operation between measurements. In this modification steps 1 and 2 of the measuring sequence commence as soon as the fuel to be measured is supplied to the engine so that a delay in operating a switch to bring in the remainder of the sequence, does not delay the completion of the sequence. When a series of octane measurements is made on a stream of fuel, as for example to monitor the stream, substantial time is saved by not having to begin a measurement sequence with stage 1. On the other hand when measurements are made after switching to new fuels, there is no need to wait for the engine to first stabilize on the new fuel inasmuch as such stabilization is generally complete by the time stage 2 terminates, and does not have to be completed until stage 3 terminates.

Further time saving can be effected by having the automatic engine compression control operating between octane measuring sequences, and with the fuel mixture automatically controlled to be on the lean side of the maximum knock ratio. This is done by modifying the stand-by operation, as by either arbitrarily returning the fuel bowl to a level from which essentially all fuels are supplied a little lean, or as by providing an automatic bowl control that cooperates with the automatic compression correction control to automatically lower the bowl after a compression correction and to repeat the bowl-down movement if the lowering results in an automatic decrease in compression. This can reduce the amount of bowl lowering needed in stage 3 of the automatic octane measuring sequence, and save time this way.

To guard against an excessively low pre-positioning of the bowl, this automatic bowl pre-positioning control can also be arranged to raise the bowl when an automatic compression-increasing signal is produced after a bowl-down step, and to repeat the upward bowl movement so long as the previous bowl-up movement results in a compression-decrease signal.

A little reduction in sequence time can also be effected by moving the compression correction stage 4 from its order between stages 3 and 5, and place it instead between stages 5 and 6. The compression ratio adjustment will still bring the compression ratio to the dead band before the intermittent small upward steps of the bowl in stage 6, but the adjustment will not have to be as large as needed when the bowl has not yet made its long first upward climb in stage 5. Less compression ratio adjustment time will accordingly be consumed.

According to another variation, the sequencer can be connected to bring the carburetor bowl to a predetermined low level, after an octane number determination is completed, so that the bowl is ready to immediately begin its upward steps for the next octane number determination. The predetermined low level can be selected as the lowest level reached by the bowl with all fuels, when it goes through the octane determining sequence illustrated in FIG. 1. This low bowl position will accordingly be at or below the level needed to start the stepwise upward movements, regardless of the fuel to be tested, and a test sequence is initiated without the delay involved in the bowl lowering.

In the last-mentioned variation automatic compression ratio adjustment can also be kept in operation to bring the test engine knock intensity within the dead band while the bowl is in its lowest or base position and before a test sequence is started. With some fuels such low bowl position may be too low for the knock intensity to reach the dead band, and the sequencer can be modified to then automatically raise the bowl enough for the knock intensity to reach the dead band. The equipment thus is made ready to start and very rapidly complete the octane-determining sequence.

The base position of the carburetor bowl in the foregoing variations can be that at which stage 5 of FIG. 1 commences, or at which stage 6 commences.

The position of the test engine's cylinder head with respect to its crankcase should be accurately measured in order to give accurate octane readouts. In accordance with the present invention it has been found highly effective to use a resistance type potentiometer, preferably with a sliding tap, as illustrated for example in FIGS. 3 and 4. The resistance element of the potentiometer is preferably of very uniform characteristics such as described in U.S. Pat. No. 4,036,786 and should have a linearity within ±0.1%.

FIGS. 3 and 4 show an upper block 201 secured by bolts 203 to the cylinder head 210 of the test engine, with a lower block 202 secured to the crankcase 211 by mounting bolts 204. Both blocks are preferably made of thermal insulation such as molded plastics, delrin (polyformaldehyde) being very effective. Grooved aluminum heat dissipation plates 206,207 are illustrated as interposed between the blocks and the engine parts to reduce the transfer of heat from the engine to the blocks.

In a pocket 208 formed on one side of block 202, potentiometer 220 is securely fixed as by a mounting strap that is not shown. The slider shaft 221 of the potentiometer projects upwardly through an aperture in a flange 224 at the top of block 202. An O-ring 225 is fitted in a groove in the aperture wall and engages shaft 221 to act as a dust seal. The shaft is also urged upwardly by a cross-bar 230 of split construction clamped around the shaft and also clamped around two spaced guide pins 231, 232. These pins project downwardly into sockets 233, 234 in block 202 while coil springs 241, 242 surround the respective pins and are compressed between the bottoms of the sockets and the cross-bar.

The top of shaft 221 is thus urged against an adjustable engagement plate 244 carried by a threaded rod 245 threadedly engaged in an upper wall 205 of block 201. Adjustment of the position of plate 244 is effected by means of a screw-driver slot 246 in the top end of the rod 245, and a locking jam nut 247 can be used to lock the adjustment.

An upward force of about $\frac{1}{2}$ pound urging shaft 221 against plate 244 holds them in firm contact notwithstanding the vibrations generated by the test engine as it operates, and causes the shaft to accurately follow all up and down movements of the cylinder head with respect to the crankcase. Leads connected to the three potentiometer terminals supply the electrical signals corresponding to the shaft position.

The blocks 201, 202 can also be fitted with one or more limit switches responsive to the travel limits of the cylinder head. As shown vertically-extending tabs 251, 252 have their upper ends secured to upper block 201 and a vertically-extending slot 253 in their lower portion. Received in this slot is a sensing arm 255 of a limit switch 257, 259 carried by the lower block 202. The slot 253 and arm 255 are so related that limit switch 257 is tripped when the cylinder head moves downwardly far enough to increase the engine's compression ratio to the point at which operation of the engine becomes risky. The tripping of the switch can be arranged to shut down the engine and/or generate a warning signal.

The second tab-and-switch assembly can be used to correspondingly react when the compression ratio of the test engine is at its low limit, or slot 253 can be dimensioned so that its lower end trips switch 259 into warning position at that limit.

Figure 4A:
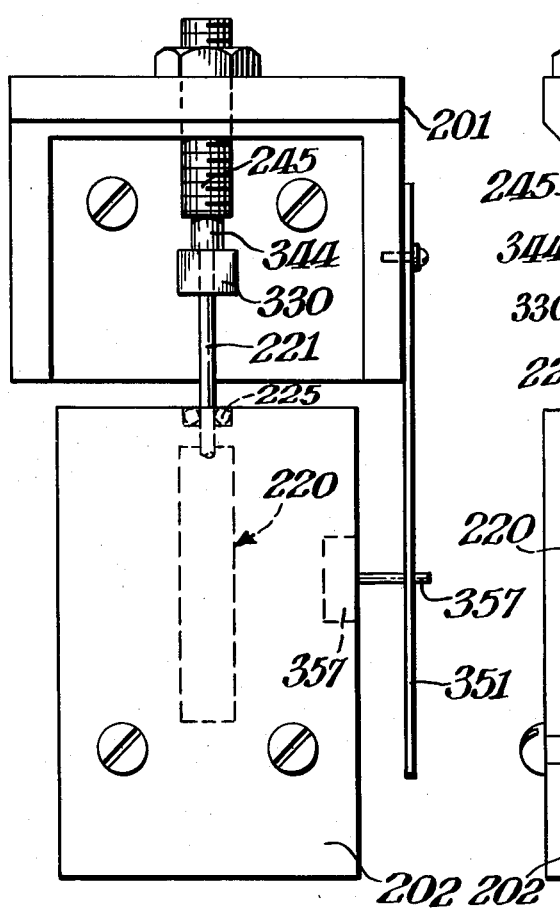
FIGS. 3A and 4A are views similar to those of FIGS. 3 and 4, of a modified test engine attachment.
Figure 3A:
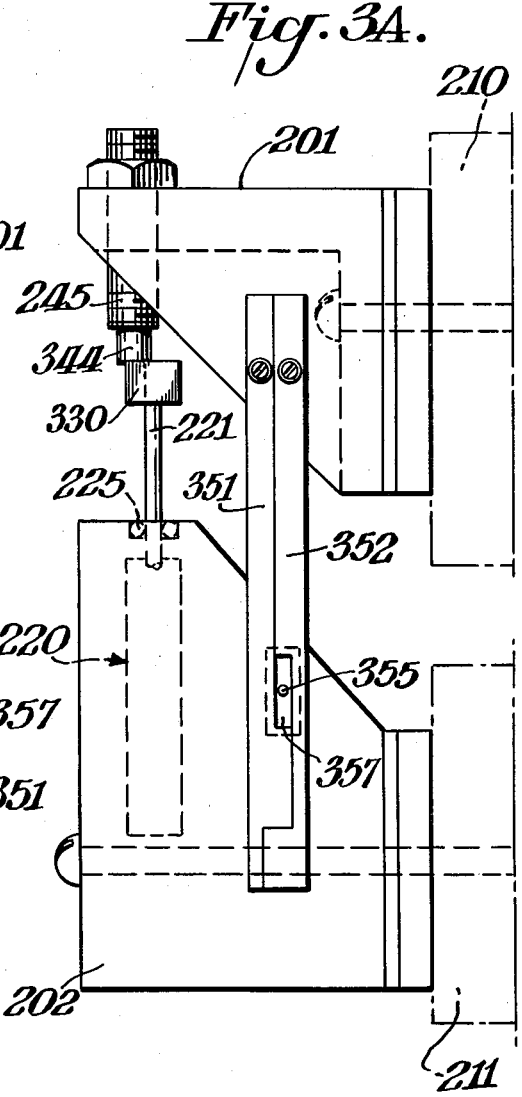

FIGS. 3A and 4A illustrate a modified attachment arrangement for coupling the cylinder height sensor (potentiometer 220) to a test engine. This arrangement can utilize the same mounting blocks 201, 202 held in place the same way as in FIGS. 3 and 4, but without the sockets 233, 234.

In place of cross-bar 230, the modified arrangement has magnetic collar 330 shrunk or threadedly secured on the upper end of slider shaft 221. This collar is magnetically attracted to a magnetic insert 344 fastened to the lower end of adjustment rod 245, the insert taking the place of engagement plate 244.

One or both of the collar 330 and insert 344 is permanently magnetized so that these two members are attracted to each other and held in contact with sufficient force to overcome the weight of slider shaft as well as the frictional resistance offered by wiper seal 225 and by the engagement of the slider shaft with the potentiometer winding. In this arrangement slider shaft faithfully follows all up and down movements of the engine cylinder 210 with respect to the crankcase 211, notwithstanding the vibrations and knocking of the test engine as it operates. Also the smaller number of moving parts and the absence of springs from the modified arrangement leaves less chance for misoperation.

While it is generally desirable to use brass or stainless steel of low magnetic permeability for metal members such as the slider shaft 221 and the threaded rod 245, one or both of them can alternatively be made of high magnetic permeability metal or high coercive force metal. In such a variation the insert 344 or collar 330 or both are not needed and the upper end of the slider shaft can directly engage the lower end of the threaded rod.

FIG. 4A also shows a single limit switch 357 operated by two control tabs 351, 352. This switch has an arm 355 that can take three positions, a central one, as illustrated, which it normally occupies, an upper one into which it is tripped by upward movement of tab 352, and a lower one into which it is tripped by downward movement of tab 351. In both of these tripped positions the switch gives warning of improper engine operation, or shuts the engine down.

Figure 2:
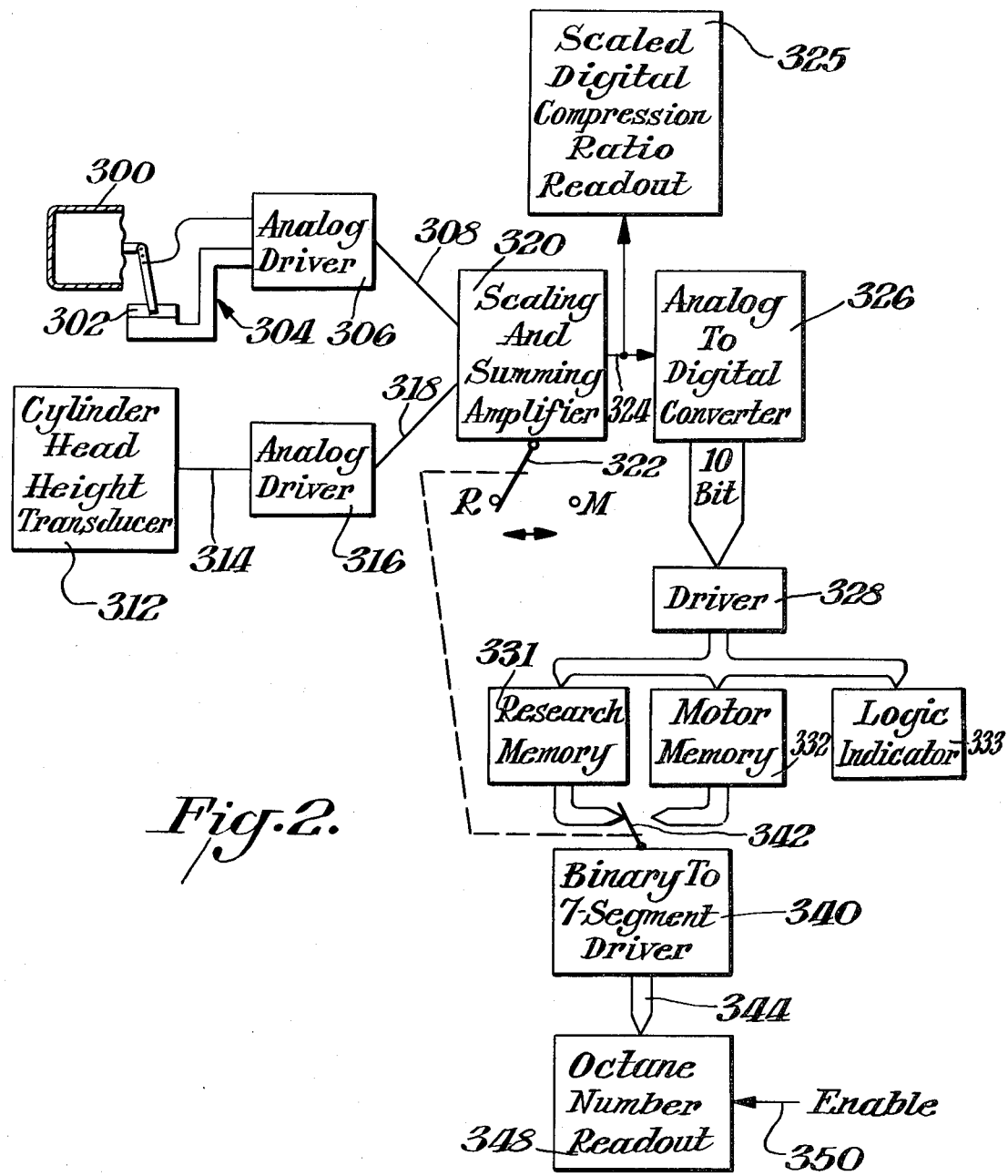
FIG. 2 is a block diagram of a numerical display arrangement for automatically displaying octane numbers under the control of the apparatus of FIG. 1.

Another feature of the present invention is that the octane number can be displayed as such rather than as a cylinder height position, and can have a built-in barometric pressure correction so that no computation is needed. FIG. 2 shows one very effective arrangement to this end.

FIG. 2 shows a barometric pressure transducer 300 connected to operate a potentiometer 302 from which output leads 304 are connected to an analog driver 306 that delivers at 308 an analog voltage corresponding to the ambient atmospheric pressure. A cylinder head height transducer 312, which can be the transducer of FIGS. 3 and 4, supplies its signal through line 314 to another analog driver 316 which delivers at 318 an analog voltage corresponding to the cylinder head height.

Both analog voltages are supplied to a scaling and summing amplifier 320 which converts them to values in appropriate scales of values suitable for combining to make the barometric adjustments described in Tables 4 and 15 (pages 31 and 62) of the above ASTM publication. Amplifier 320 is connected to sum the scaled values in two different ways, in accordance with the Research Octane barometric correction (Table 4) or the Motor Octane barometric correction (Table 15), and a settable selector 322 determines which way the correction is applied.

The corrected signals are then supplied by line 324 to an analog-to-digital converter 326 which delivers corresponding 10-bit binary coded decimal signals through driver 328 to a Research memory comparator 331, a Motor memory comparator 332, and a logic indicator 333. Comparator 331 contains a memory in which is stored the octane number values for each 10-bit signal that can be obtained by the Research octane determining method, and comparator 332 a memory storing the octane number values for each 10-bit Motor octane signal. Indicator 333 is not needed; it merely provides an L.E.D. display of the 10-bit signals so that this can be checked in the event misoperation is suspected. Logic indicator 20 of FIG. 1 serves the same purpose. A memory bank of only about 4000 words or 16,000 bits is adequate for each comparator.

A binary-to-7-segment driver 340 has a selector 342 coupled with selector 322 and arranged to receive the output of comparator 331 or 332 and to deliver through its own output 344 a 7-segment signal to a 7-segment readout unit 348. An enable line 350 energized by the O-output of Sequencer 70 of FIG. 1, illuminates or exposes the 7-segment readout, and can also sound an audible signal such as a gong to announce the completion of a test sequence. The octane number can also be supplied by output 344 to a printer for automatic recording, and/or to a computer for storage and subsequent reference. It is sometimes helpful to make automatic records of entire test sequences on a time scale showing the compression ratio values at various stages of each sequence, and thus be able to check back and verify that there was no equipment misoperation and the final octane number readout is a valid test result.

If desired the apparatus of FIG. 2 can also be provided with a separate readout 325 to show compression ratio of the test engine, with or without the barometric correction. Such a readout is obtained by rescaling the output of amplifier 320 or the output of driver 316.

The above-described apparatus can be fitted to a test engine without interfering with the manual operation of the engine. Thus when the apparatus is in stand-by condition the compression ratio of the test engine can be changed by operating the manual change control 60. Test engines usually have several carburetor bowls that can be selectively used to supply fuel and only one of the bowls need be equipped with the automatically controlled bowl motor. In addition the bowl motor can also be supplied with a manual control so that its bowl can be raised or lowered at will.

A stand-by switch can also be provided and connected to supply a momentary reset signal to line 74 and thus shift the apparatus to stand-by operation in the event it is operating in the automatic octane determining mode.

The various electrical components of the apparatus of the present invention can use standard off-the-shelf components connected in a manner that is clear from the above description. The Compression Correction Pulse Generator 28 is illustrated in greater detail in FIG. 5, although other constructions can be utilized.

FIG. 5 shows the Compression Correction Pulse Generator within the dash-line outline 28, and also shows timing pulse generator 44 connected to it. The heart of generator 28 is a standard pre-settable counter 140 in integrated circuit form designated CD 40103, having its pins 4, 5, 6, 7, 10, 11, 12 and 13 connected to receive the respective bit signals of the 8-bit knock intensity error generator 30. Pin 9 is a jamming or locking connection that receives the timing pulses from the timer 44, each timing pulse causing the counter 140 to fix or lock in the error bit count at that instant. Pin 14 of the counter delivers an output signal whenever an error count of any magnitude (not zero) is thus fixed.

Timing pulses are also delivered by line 45 to pin 3 of counter 140, and these pulses illustrated at 142 temporarily block the counting function of the counter for the duration of each short timing pulse. When not locked, the counting function of counter 140 is actuated by supplying to its pin 1 the counting pulses delivered by an oscillator 145 shown as integrated circuit CD 4098. Each such counting pulse counts down one from the error signal that was locked in counter 140 when its pin 9 was activated, but this count-down does not commence until after the completion of the short timing pulse that blocked the counting. The count lock-in does not require continued activation of pin 9, but is reduced by the counting action, and whether or not reduced to zero is switched to a new lock-in or fix when the next timing pulses reaches pin 9. The new lock-in corresponds to the bit error signal at the commencement of that timing pulse.

Oscillator 145 is arranged for oscillation to generate square wave counting pulses at two different periods such as 0.04 and 0.01 seconds, respectively. These counting pulses are generated at pins 10 and 12 of oscillator 145 when its pin 4 is activated, and the counting pulse period is determined by the presence or absence of activation in line 146. Such activation is independently effected by lines 106 and 107 (FIG. 1). When neither 106 nor 107 is activated, oscillator 145 generates its counting pulses as the longer period, so that the error signal count-down in counter 140 takes a relatively long time. The largest error signals can be such that this slow count-down takes up all the time between timing pulses 142, or even requires more time.

Pin 14 of counter 140 remains activated during the entire count-down, and only becomes deactivated when the count-down reaches zero. Activation at this pin delivers a signal through an OR gate 148 which can be type CD 4071, and lead 149, to AND gates 151, 152 and 153. A similar timing pulse signal is delivered from line 145 through the OR gate to the same AND gates.

AND gate 153 which can be type CD 4081, is shown as having two inputs, one from line 45 and the other from output pin 9 of oscillator 145. With that oscillator connected as shown, this output pin is energized once each oscillation period, and energization delivered by the OR gate to lead 149 will then cause the square wave counting pulses to be generated at output pins 10 and 12 of the oscillator. Thus the initiation of a timing pulse 142 will initiate the counting pulses and they will continue as long as any error locked into counter 140 is not fully counted down. For the duration of the initiating timing pulse the counting pulses are ineffective to count down the error, because any reduction in the locked-in error signal is blocked by the activation of pin 3 in the counter.

At the termination of the initiating pulse the countdown becomes effective and if it reaches zero before the next timing pulse, AND gate 153 stops passing a signal so that the counting pulses stop. If the count-down does not reach zero by the time the next timing pulse arrives, the counting pulses continue but become ineffective by the blocking action of the timing pulse at pin 3 of the counter and at the same time the error signal being then received by the counter from the error bits is locked in the counter. Upon the termination of the new timing pulse, count-down of the newly locked-in error signal will proceed unless the newly locked-in signal is zero.

The energization delivered to lead 149 is a continuous motor-control pulse initiated by the initiation of a timing pulse 142 and terminated when the error signal is counted down to zero, or when the timing pulse terminated if the error signal is then zero. This motor-control pulse is delivered to AND gates 151 and 152 and when appropriate passed to the proper winding of the compression ratio control motor on the test engine. Such passage is determined by the condition of the knock intensity signal. AND gate 151, which can be a duplicate of AND gate 153, has two input leads one of which, 156, is connected to high output 34 (FIG. 1) of the above-dead-band detector. The other input lead of gate 151 is lead 149 and motor-control pulses are accordingly passed to compression decrease output lead 161 of gate 151 only when the knock intensity is above the selected dead-band.

On the other hand such motor-control pulses are only passed to compression increase output 162 of AND gate 152 when the knock intensity is below the dead-band and the compression is to be increased. To this end AND gate 152 is a four-input gate, type CD 4082, one of the inputs, 157, being connected to low output 36 of below-dead-band-detector 22. Another input 158 is connected through inverter 168 to line 146, and a third input 159 through invertor 169 to line 83 (FIG. 1). The fourth input is from lead 149.

When neither lead 146 nor lead 83 is energized, both inputs 158 and 159 are energized so that compression ratio increases are controlled in a manner correlative to the manner compression ratio decreases are controlled. However energizing line 83 (at step 3 of sequencer 70) causes lead 159 to become de-energized so that compression increase signals are blocked. Also when line 146 is energized lead 158 becomes de-energized and again compression increase signals are blocked. As pointed out above, energizing lead 146 also shifts the oscillator 145 to its short-period oscillation so that error count-down becomes much faster and compression control pulses much shorter. It is preferred that these short pulses be no longer than about 3 seconds when the error signal is at its maximum and that apart from the fraction of a second needed for the compression control signal to prepare the compression change motor for actually increasing the compression ratio, the compression control signal vary in duration with the magnitude of the locked-in error, the minimum control signal being sufficient to move the test engine cylinder about 0.3 mil or increase the compression ratio about ½ a compression ratio number. These numbers indicate cylinder positions and can range from 172 to 1195.

Inventors 168,169 can both be type CD 4049, and timing pulse generator 44 can be an oscillator type CD 4098, like oscillator 145.

In many cases the barometric connection arrangement of FIG. 2 can be simplified by constructing it with only a Research Octane correction or only a Motor Octane correction, and eliminating switches 322, 342. Both connections can be used with any Octane Test engine where an extremely versatile test engine installation is desired, but it is generally too awkward to make the many manual adjustments needed to convert a test engine set-up from Research Octane determining operation to Motor Octane determining operation. To avoid such awkwardness separate test engines are frequently used, one permanently set up for Research Octane determinations, and the other for Motor Octane determination. Each set-up can have its own automatic controller of FIG. 1, but needs only one type of barometric correction and one of the memories 331, 332.

Obviously many modifications and variations of the present invention are possible in the light of the above teachings. It is, therefore, to be understood that within the scope of the appended claims the invention may be practiced otherwise than as specifically described.

What is claimed is:

1. An all-electronic controller for responding to error signals, said controller including
   (a) a receiving unit for receiving and periodically locking in a digital error signal,
   (b) a counting unit connected to count down the error signal after it is locked in,
   (c) a control circuit connected to deliver one output signal during the error count-down and to deliver another output signal when the error count-down reduces the locked-in error to zero, and
   (d) shift means connected for external actuation to shift the count-down from a high count rate to a low count rate, the receiving unit is connected to an octane test engine knock signal output, and the control circuit is connected to deliver its output signals to the compression ratio change actuator of the test engine.

2. The combination of claim 1 in which the controller also has an externally-actuated inhibitor input connected to inhibit the delivery of one of the control output signals notwithstanding an error signal calling for such output.

* * * * *

UNITED STATES PATENT AND TRADEMARK OFFICE
CERTIFICATE OF CORRECTION

PATENT NO. : 4,366,701
DATED : January 4, 1983
INVENTOR(S) : JOHN M. BITTNER

It is certified that error appears in the above-identified patent and that said Letters Patent are hereby corrected as shown below:

Column 2, line 64, "compres" should be --compares--;

Column 4, line 18, "knock error" should be --knock intensity error--;

Column 13, line 21, "pulses" should be --pulse--;

line 33, "as" should be --at--;

line 44, "145" should be --45--; and

Column 14, line 55, "Inventors" should be --Invertors--.

Signed and Sealed this

Tenth Day of May 1983

[SEAL]

Attest:

GERALD J. MOSSINGHOFF

Attesting Officer

Commissioner of Patents and Trademarks